United States Patent [19]

Tanimoto et al.

[11] Patent Number: 4,893,512
[45] Date of Patent: Jan. 16, 1990

[54] SWINGING-TYPE AUTOMATIC EXAMINATION APPARATUS FOR PIPING

[75] Inventors: Kenichi Tanimoto, Ibaraki; Osamu Kakuma, Uozu, both of Japan

[73] Assignees: Doryokuro Kakunenryo Kaihatsu Jigyodan; Sugino Machine Limited, both of Japan

[21] Appl. No.: 196,172

[22] Filed: May 17, 1988

[30] Foreign Application Priority Data

Jun. 12, 1987 [JP] Japan .................. 62-146437

[51] Int. Cl.⁴ ........................................... G01N 29/04
[52] U.S. Cl. ....................................... 73/622; 73/637; 73/638
[58] Field of Search .................. 73/622, 637, 638, 640; 376/248, 249, 250, 251, 252; 165/11.1, 11.2

[56] References Cited

U.S. PATENT DOCUMENTS 3,984,008 10/1976 Syun-ichi et al. .................. 165/11.2
4,018,345 4/1977 Formanek et al. .................. 165/11.2
4,345,658 8/1982 Danel et al. .......................... 376/249

Primary Examiner—John Chapman
Assistant Examiner—Louis M. Arana
Attorney, Agent, or Firm—Armstrong, Nikaido, Marmelstein, Kubovcik & Murray

[57] ABSTRACT

A swinging-type apparatus for automatically examining pipes includes first and second clamping devices provided at the ends of an extendible body. The first clamping device is made to clamp a first pipe, the second clamping device is made to unclamp the first pipe, is lifted up away from the first pipe, swung to an adjacent second pipe to be examined, lowered down to the second pipe and made to clamp the same. Next, the first clamping device is made to unclamp the first pipe, is lifted up away from the first pipe, swung to the second pipe, lowered down to the second pipe and made to clamp the same. Sensors provided on at least one of the clamping devices then examine the second pipe. By repeating these operations, the apparatus can be made to travel from one pipe to another to examine a cluster of pipes. The apparatus can also be made to move along a pipe axially thereof by extending and shortening the length of the extendible body.

9 Claims, 9 Drawing Sheets

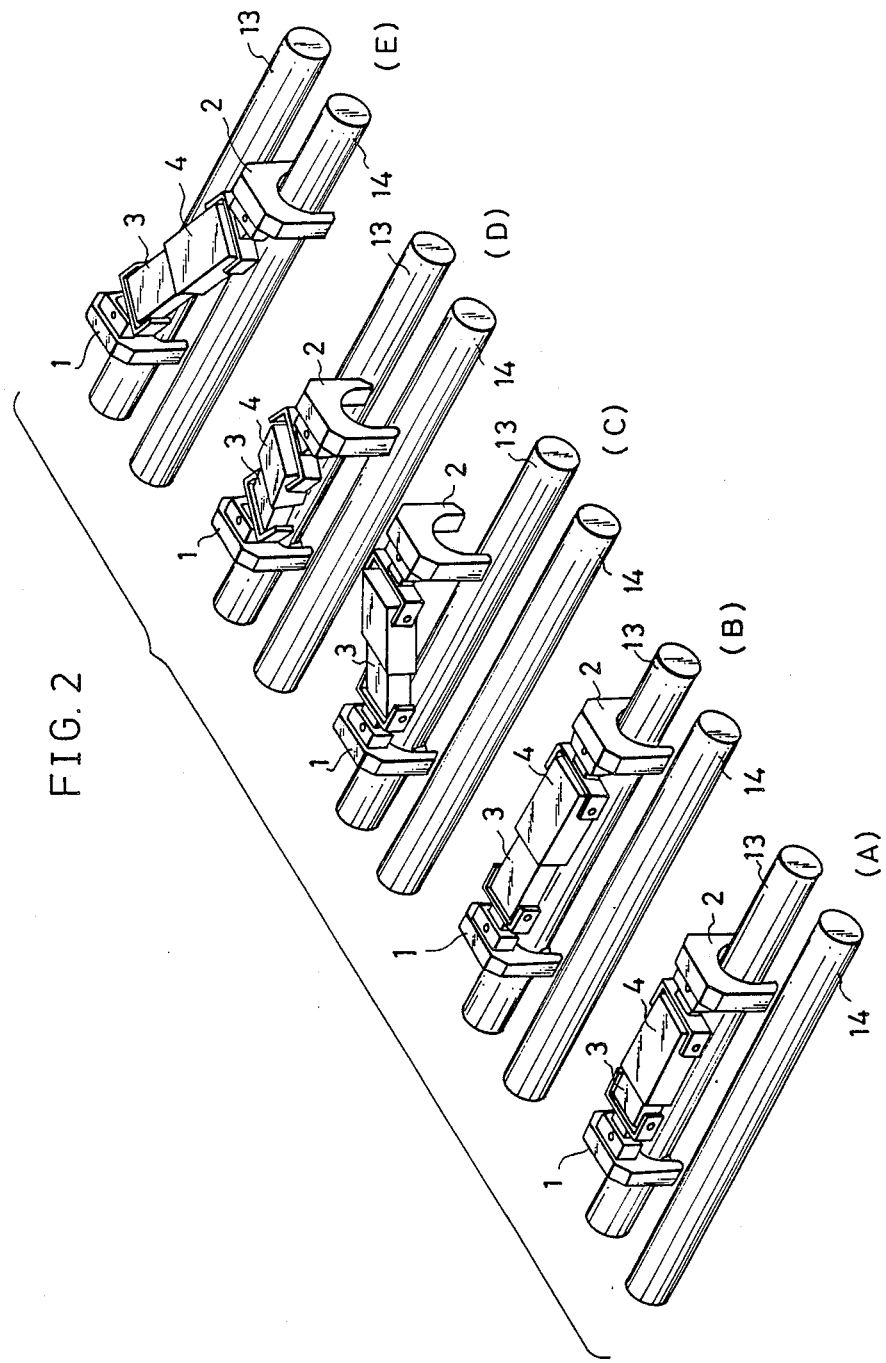

FIG. 3
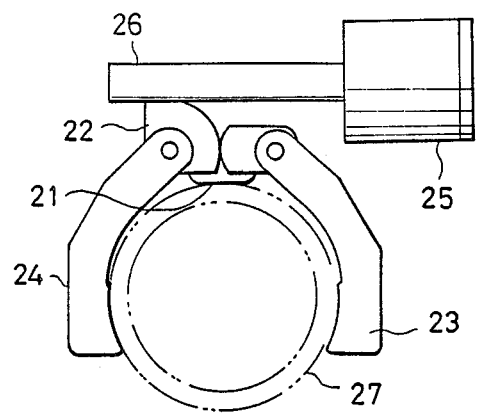
FIG. 4(A)
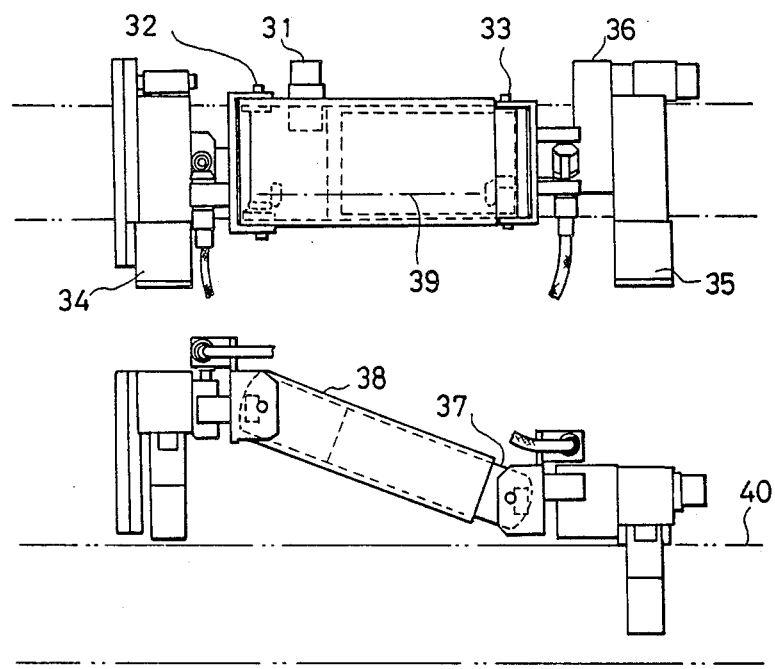
FIG. 4(B)

FIG. 6(A)
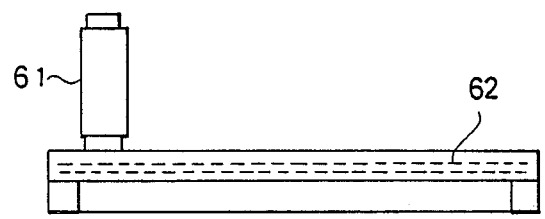
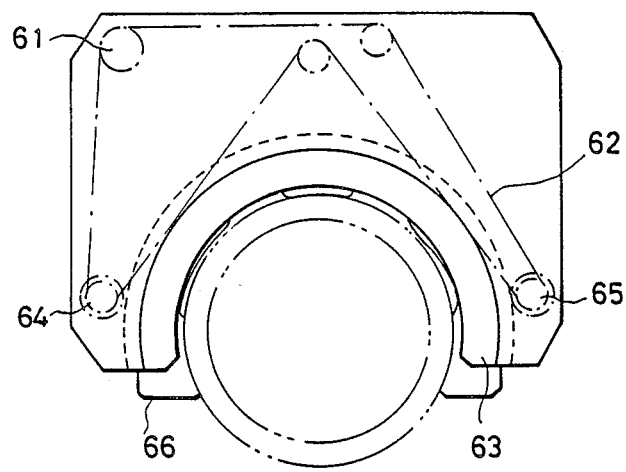
FIG. 6(B)

SWINGING-TYPE AUTOMATIC EXAMINATION APPARATUS FOR PIPING

BACKGROUND OF THE INVENTION

This invention relates to a piping examination apparatus for the maintenance and inspection of a number of closely clustered pipes. More particularly, the invention relates to a swinging-type automatic examination apparatus for automatically examining piping while "walking" across the narrow spaces between pipes.

Nuclear reactors are subjected to periodic examination to verify the safety of the equipment. Since the examination of the primary system of a nuclear reactor is an operation performed in a radioactive environment peculiar to nuclear power plants, reducing the exposure of the examination personnel to radiation and shortening the time required for the examination are important considerations. Accordingly, use is made of a remotely controlled mobile apparatus equipped with sensors.

FIG. 8 is a perspective view illustrating the primary cooling system of an advanced thermal reactor. Numeral 81 denotes a nuclear reactor, 82 a pressure tube assembly, 83 a calandria tank, 84 one of more than 200 inlet pipes, 85 one of more than 200 outlet pipes, 86 a steam drum, 87 a main steam pipe, 88 a descending pipe, 89 a recirculation pump, and 90 a lower header.

The outlet pipes 85 of the reactor 81 have a little less than 3000 welding seams, and the inlet pipes 84 have a little more than 4000 welding seams, for a total of about 7000 welding seams. The outlet pipes 85 constituted by a group of small-diameter pipes are arranged at a pitch of 240 mm×150 mm—250 mm at the horizontal portions and at a pitch of 410 mm around the steam drum 86 and at the vertical portions. The inlet pipes 84 are arranged at a pitch of 200 mm×120 mm—250 mm at the horizontal portions and at a pitch of 200 mm around the lower header 90 and at the vertical portions. Thus, there is not enough space between the inlet and outlet pipes to allow an examiner to approach and inspect them, and the radiation level surrounding the piping is comparatively high. Accordingly, there is a need to develop a remotely controlled, automatic examination apparatus for the purpose of reducing exposure to radiation, shortening the time required for the examination and enlarging the examination region to include the spaces among the innermost pipes.

In the development of methods and apparatus for examining these inlet and outlet pipes, these pipes were considered to be obstacles to examination. However, a remotely controlled, automatic examination system has been tested and developed which uses the inlet and outlet piping as a foothold for an examination device and is adapted to wander along and across the pipes automatically by being remotely controlled.

FIG. 9 is a view illustrating the overall arrangement of this remotely controlled, automatic examination system for examining outlet pipes, and FIG. 10 is a view illustrating the system in which a mobile unit included in the system "walks" from one outlet pipe to another for examining the same. Numeral 91 denotes a control unit, 92 a data display unit, 93 a remotely controlled mobile unit, 94, 95, 9 pipes, 97, 98 yokes, 99–102 clamping devices, and 103 an arm.

In FIG. 9, the remotely controlled unit 93 is remotely controlled by the control unit 91 and is adapted to slide along piping, walk from one pipe to another in a direction perpendicular to the pipes, and examine a pipe while clamped thereto. Data indicative of the position of the mobile unit 93 of the examination system and the results of examination are displayed by the display unit 92 and stored in memory.

The operation of the remotely controlled mobile unit 93 will now be described with reference to FIG. 9.

The clamping devices 99, 100 are provided on the ends of the yoke 97, and the clamping devices 101, 102 are provided on the ends of the yoke 98, the clamping devices having the same spacing between them as the pipes. The distal ends of the clamping devices 99–102 open and close in response to control signals from the control unit 91 to grasp and release the pipes. The yokes 97, 98 are interconnected by an arm 103. With the point at which one yoke is connected to the arm 103 serving as a center, the other yoke swings about this center so as to describe a semicircle the radius of which is the length of the arm 103.

In the state shown at (A) of FIG. 10, the clamping devices 99, 100 and 101, 102 of the yokes 97 and 98 are situated on the pipes 94, 95 and are clamping these pipes. Next, at (B) of FIG. 10, the clamping devices 99, 100 are opened and the yoke 97 is swung so as to describe a semicircle about the point at which the yoke 98 is connected to the arm 103. The clamping devices 99, 100 then move onto the two mutually adjacent pipes 95, 96 and are closed to clamp these pipes, as shown at (C) of FIG. 10. Next, the clamping devices 101, 102 are opened and the yoke 98 is swung so as to describe a semicircle about the point at which the yoke 97 is connected to the arm 103, as illustrated at (D) of FIG. 10. The clamping devices 101, 102 then move onto the two mutually adjacent pipes 95, 96 and are closed to clamp these pipes, as shown at (E) of FIG. 10. Thereafter, these operations are repeated so that the mobile unit 93 can be moved to any desired piping position.

In the state shown at (A) or (E) of FIG. 10, the clamping devices 99, 100 are opened and a sliding device 104 is driven into operation to advance the yoke 98 a prescribed stroke (10 mm in the test apparatus) axially of the piping and then stop the yoke, after which the clamping devices 99, 100 are closed.

Next, the clamping devices 101, 102 are opened and the sliding device 104 is driven into operation again to advance the yoke 97 the prescribed stroke axially of the piping (in the direction of yoke 98) and then stop the yoke, after which the clamping devices 101, 102 are closed.

The mobile unit 93 can thus be moved axially of the piping by repeating these operations. Furthermore, since the foregoing motions can be reversed, the mobile unit can be advanced in either direction along the pipes.

Though the sliding stroke is 10 mm in the test apparatus, the sliding stroke can be lengthened to make possible a longer range of movement covered by one operation.

Thus, after a worker mounts the mobile unit at an initially set position, the mobile unit is made to repeat the foregoing operations by remote control, thereby being made to walk across and slide along the pipes automatically while examining the pipes. Then, when the entire examination procedure ends, the mobile unit 93 is made to move in the opposite direction in order to return to the initially set position.

However, since the remotely controlled mobile unit 93 requires a travelling space around the pipes which includes the height of the unit itself, e.g. a space of about 500 mm in the case of outlet pipes 85, it is difficult to apply the unit to the narrow confines among the innermost outlet pipes 85 in the spaces surrounding the horizontal portions of the pipes.

SUMMARY OF THE INVENTION

Accordingly, an object of the present invention is to provide a swinging-type automatic piping examination apparatus capable of moving among pipes, irrespective of the accuracy of the pitch at which the pipes are attached and even if the pitch differs, which apparatus makes it possible to widen the area of examination by enabling examination to be performed in the narrow spaces among pipes where the radiation level is comparatively high.

According to the present invention, the foregoing object is attained by providing a swinging-type automatic examination apparatus for piping, which comprises: first and second clamping devices for clamping and releasing pipes; an extendible body provided between the first and second clamping devices and mechanically connected to them so as to be capable of moving horizontally and vertically; an examining device provided on at least one of the clamping devices for scanning and examining a pipe surface; and driving means for driving the first and second clamping devices, the extendible body and the examining device; wherein when the driving means is actuated to move the examination apparatus, the examination apparatus is made to travel among and examine a group of pipes by successively repeating a series of operations in which the first clamping device is made to clamp a first pipe, the second clamping device is made to unclamp the first pipe, is lifted up away from the first pipe, swung to an adjacent second pipe to be examined, lowered down to the second pipe and made to clamp the second pipe, the first clamping device is then made to unclamp the first pipe, is lifted up away from the first pipe, swung to the second pipe, lowered down to the second pipe and made to clamp the second pipe.

BRIEF DESCRIPTION OF THE DRAWINGS

FIG. 3 is a front view illustrating a clamping mechanism;

FIG. 4 is useful in describing a lifting mechanism, in which (A) is a plan view and (B) a side view;

FIG. 6 is useful in describing an X-axis drive mechanism for driving various sensors, which are provided on an examining device, in the circumferential direction of a pipe, in which (A) is a front view and (B) a plan view;

DESCRIPTION OF THE PREFERRED EMBODIMENT

An embodiment of the present invention will now be described with reference to the drawings.

Figure 1:
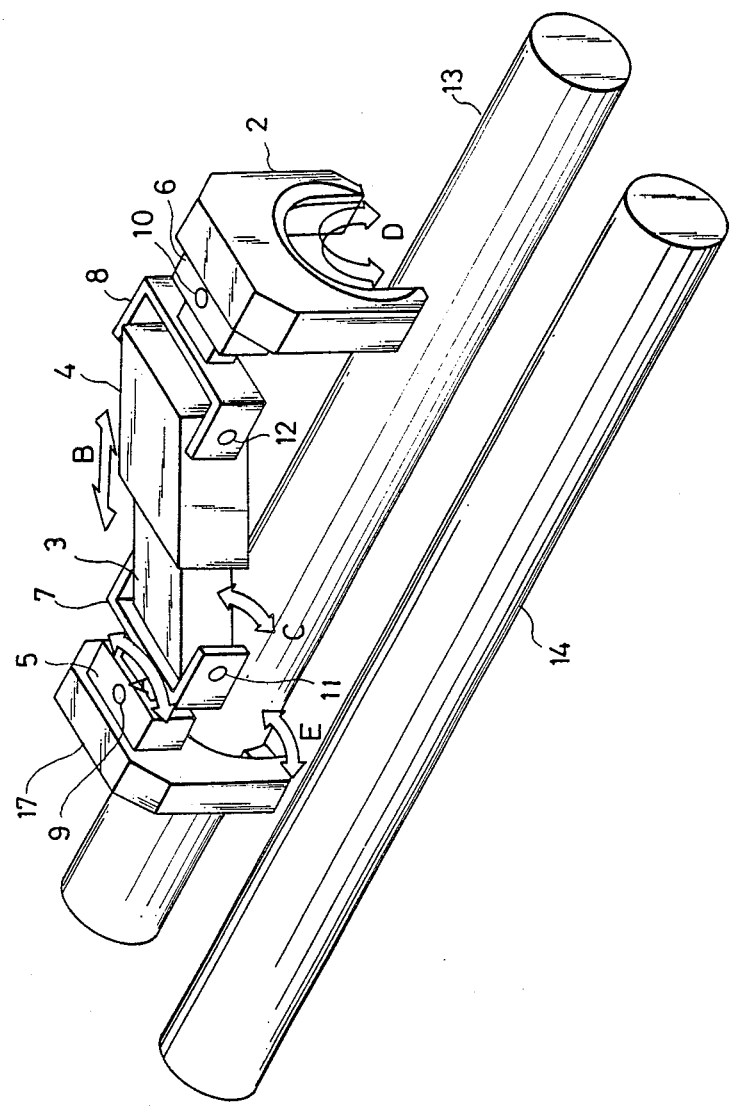
FIG. 1 is a perspective view illustrating an embodiment of a swinging-type automatic examination apparatus for piping in accordance with the present invention.
Figure 2:
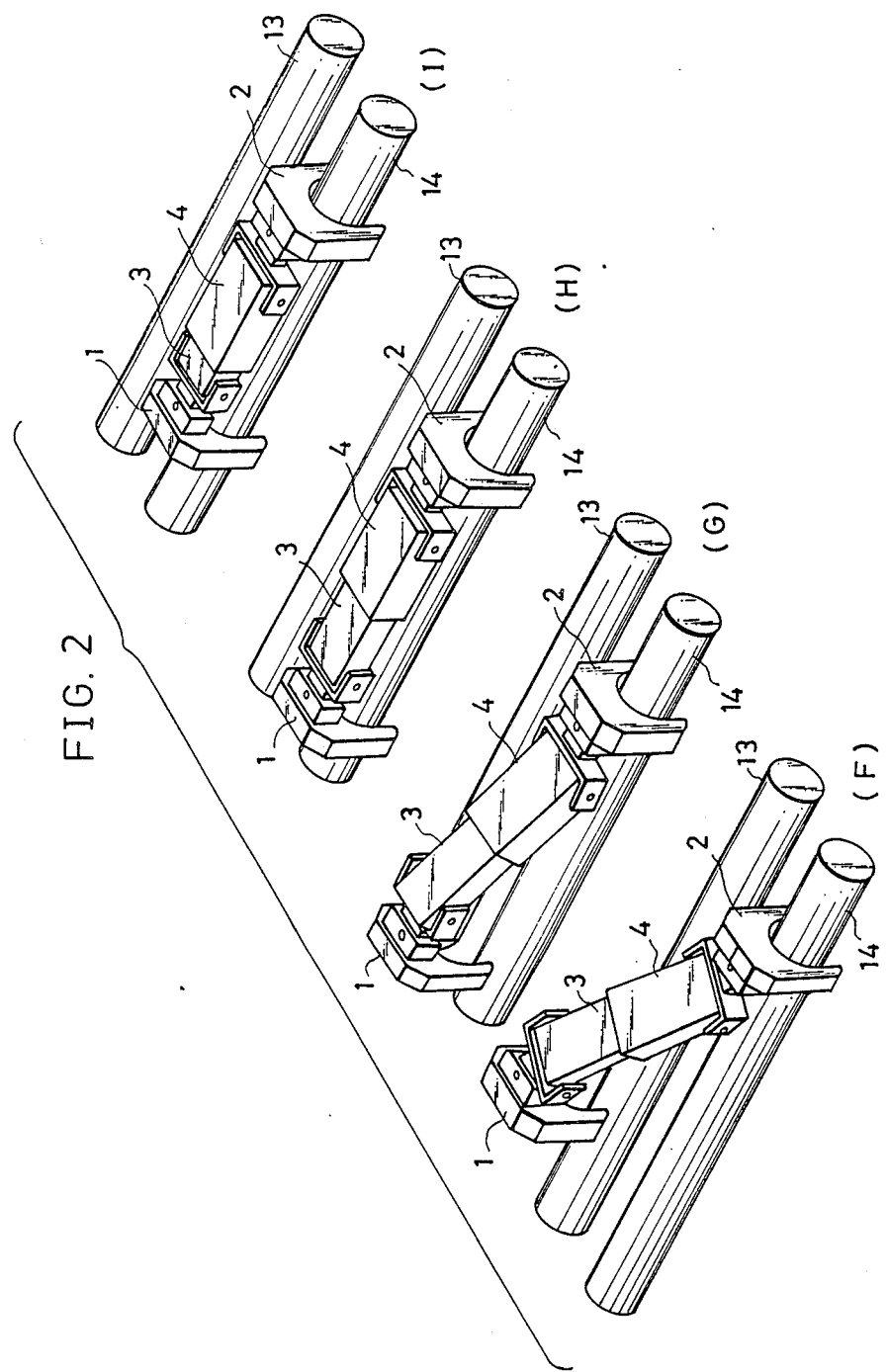
FIGS. 2(A)-2(I) illustrates the manner in which the apparatus of FIG. 1 "walks" from one pipe to another.

FIG. 1 is a perspective view illustrating an embodiment of a swinging-type automatic examination apparatus for piping in accordance with the present invention, and FIG. 2 illustrates the manner in which the apparatus of FIG. 1 "walks" from one pipe to another.

As shown in FIG. 1, the apparatus includes a clamping devices 1, 2, bodies 3, 4, gear boxes 5, 6, couplings 7, 8, swing shafts 9, 10, and lift shafts 11, 12. Numerals 13, 14 denote piping.

The clamping devices 1, 2 are connected to the bodies 3, 4 via the gear boxes 5, 6 and couplings 7, 8, respectively. As will be described below, the clamping devices 1, 2 are driven in the direction of an arrow E to clamp or release piping, and are capable of being rotated in the direction of an arrow A relative to the bodies 3, 4 about the swing shafts 9, 10, respectively. The bodies 3, 4 are supported by the respective couplings 7, 8 so as to be rotatable in the direction of an arrow C about the respective lift shafts 11, 12, and are slidable relative to each other in the direction of an arrow B (the Y direction) so that the combination of these bodies 3, 4 can be extended and retracted. Further, as will be described below, various sensors (not shown) for piping examination are provided on the side of at least one of the clamping devices 1, 2. These sensors are adapted to be driven in the direction of an arrow D (the X direction) to examine the surfaces of piping, the volume of the piping, etc.

A case will now be described with reference to FIG. 2 in which the piping examining apparatus constructed as set forth above is moved from piping 13 to piping 14 when examination of piping 13 ends.

First, the clamping device 1 is clamped and the clamping device 2 is unclamped [FIG. 2(A)], after which the body 4 is slid away from the body 3 to extend the length of the apparatus [FIG. 2(B)]. The bodies 3, 4 are then lifted up and fixed [FIG. 2(C)], and both bodies are swung to the side by amount equivalent to the pitch or spacing between pipes [FIG. 2(D)]. Next, the clamping device 2 is lowered down to the piping 14 and is caused to clamp the piping [FIG. 2(E)]. The clamping device 1 is then unclamped and the bodies 3, 4 are lifted up from the piping 13 and fixed [FIG. 2(F)], and both bodies are swung to the position of the piping 14 [FIG. 2(G)]. Next, the clamping device 1 is lowered down to the piping 14 and is caused to clamp the same after the length of the apparatus is shortened by sliding one of the bodies [FIGS. 2(H), (I)]. This ends the movement of the apparatus.

The scanning of the sensors in the circumferential direction of the piping is carried out by an X-axis drive mechanism (described below) provided on at least one of the clamping devices. Scanning axially of the piping is carried out by a Y-axis drive mechanism (described below) after one of the clamping devices is made to unclamp the piping. The position of the apparatus axially of the piping is corrected by causing one of the clamping devices to unclamp, extending the bodies a required distance in the axial direction by the Y-axis drive mechanism, causing the one clamping device to clamp the piping, causing the other clamping device to unclamp, shortening the length of the bodies and then causing the other clamping device to clamp the piping.

The apparatus can be moved along the piping axially thereof by repeating these operations.

The various components of the apparatus will now be described in greater detail.

FIG. 3 is a sectional view illustrating an embodiment of the clamping mechanism, in which numeral 21 denotes a fixing claw, 22 a gear, 23 and 24 clamping claws, 25 an air cylinder, 26 a rack shaft, and 27 piping.

The clamping mechanism is of the type in which the single air cylinder 25 reciprocates the rack shaft 26, which is in mesh with the gear 22, thereby operating the two clamping claws 23, 24 to clamp and unclamp the piping 27. More specifically, the clamping mechanism is provided at the two ends of the examination apparatus, which is fixed to the piping 27 by causing the two clamping claws 23, 24 in each clamping mechanism to clamp the piping, the claws 23, 24 being actuated via the single fixing claw 21 and the gear 22.

As mentioned above, the clamping claws 23, 24 are driven by the air cylinder 25 via the rack shaft 26. The completion of a clamping operation is verified by microswitches (not shown) attached to the clamping claws. The arrangement is such that if the pneumatic pressure source for the air cylinder 25 driving the clamping claws 23, 24 is lost when the apparatus is traveling from one pipe to another or performing an examination, the clamped state will be maintained by means of a spring (not shown) within the cylinder.

FIG. 4 is a view for describing a lifting mechanism, in which (A) is a plan view and (B) a side view. Numeral 31 denotes a DC motor, 32 and 33 lift shafts, 34 and 35 clamping devices, 36 a gear box, 37 and 38 bodies, 39 a spline shaft, and 40 piping.

The lifting mechanism of the present embodiment is of the spline drive type, in which a driving force from the DC motor 31 is transmitted to the spline shaft 39 to rotate the lift shafts 32, 33 on both sides. The bodies 37, 38 are lifted up or lowered down by the output shaft of the DC motor 31 via a gear. At such time the lift shafts 32,33 connected by the spline shaft 39 rotate through the same angle in mutually opposing directions to perform the lifting or lowering operation.

Figure 5:
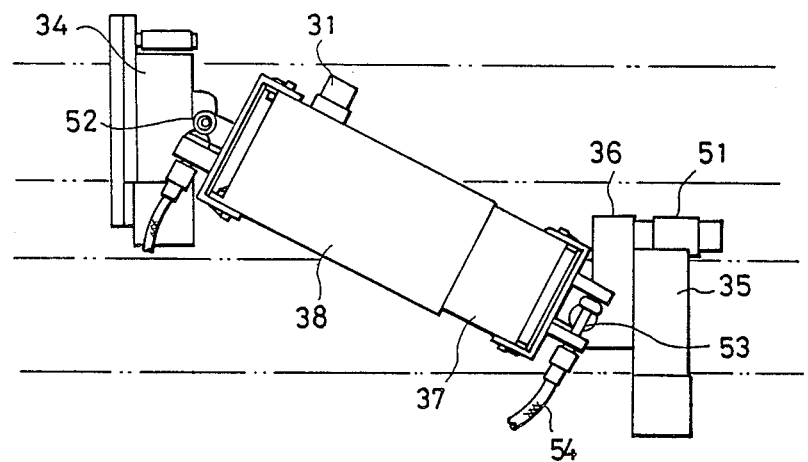
FIG. 5 is useful in describing a swinging mechanism.

FIG. 5 is a view for describing a swinging mechanism. Portions similar to those shown in FIG. 4 are designated by like reference characters. Numeral 51 denotes a DC motor for swinging, 52 and 53 swing shafts, and 54 a flexible shaft.

The swinging mechanism of the present embodiment is of the flexible shaft drive type, in which the swing shafts 52, 53 are rotated by the flexible shaft 54 driven by the DC motor 51. More specifically, the swing shaft 53 is rotated by the output shaft of the DC motor 51 via the gear box 36. The other swing shaft 52 receives driving force through the flexible shaft 54 and is rotated through the same angle as the swing shaft 53 but in the opposite direction.

The apparatus is swung by an amount equivalent to one pitch of the inlet and outlet pipes by this swinging operation. The swinging position is detected by an encoder (not shown) which rotates at a predetermined ratio with the swing shafts 52, 53. The encoder outputs a pulse signal, which is indicative of the swinging position, to a control unit where the position is digitally displayed by a display device on a control panel. The apparatus can be made to "walk" from one pipe to another in a group of pipes by using the swinging and lifting mechanisms in combination.

FIG. 6 is useful in describing the X-axis drive mechanism for driving various sensors, which are provided on the examining apparatus, in the circumferential direction of a pipe, in which (A) is a front view and (B) a plan view. Numeral 61 denotes a DC motor, 62 a timing belt, 63 a C-gear, 64 and 65 pinions, and 66 a clamping claw.

The X-axis drive mechanism of this embodiment is of the timing belt drive type, in which the C-gear 63 is rotated by the two pinions 64, 65 receiving driving force from the output shaft of the DC motor 61 via the timing belt 62. The arrangement is such that at least one of the pinions 64, 65 will be meshing with the C-gear 63 regardless of the position of the C-gear 63. Rotation is possible through 370° (10° lap) in the direction of the X axis, and the rotational speed (peripheral speed) is e.g. 100–500 mm/min. The end of the X-axis stroke is decided by automatically halting motion along the X axis in response to actuation of a microswitch by a dog, which has the C-gear 63 attached thereto, acting through a lever. The position along the X axis is detected by an encoder mounted on the rearward portion of the DC motor 61. A pulse signal from the encoder is applied to the control unit, where the position is digitally displayed by a position display device on the control panel.

Figure 7:
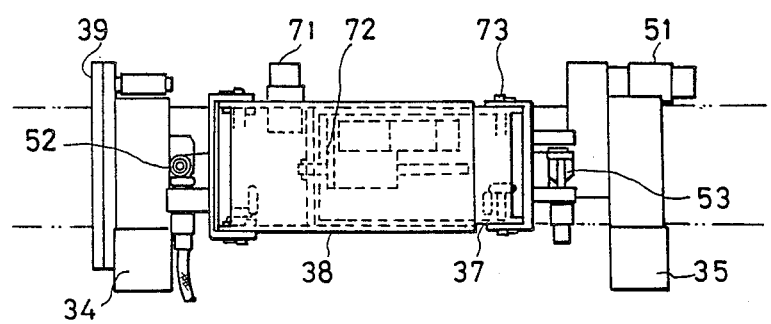
FIG. 7 is a view useful in describing a Y-axis drive mechanism for drive axially of a pipe.
Figure 8:
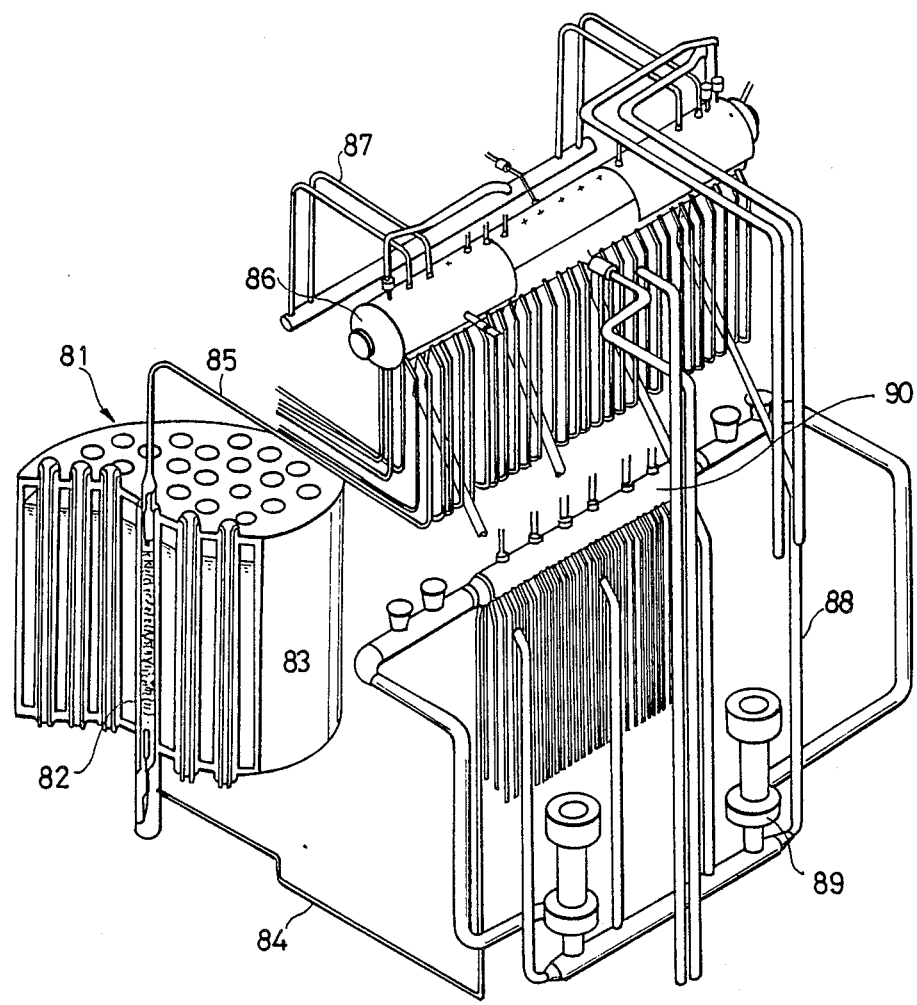
FIG. 8 is a perspective view illustrating a primary cooling system of a nuclear reactor.
Figure 9:
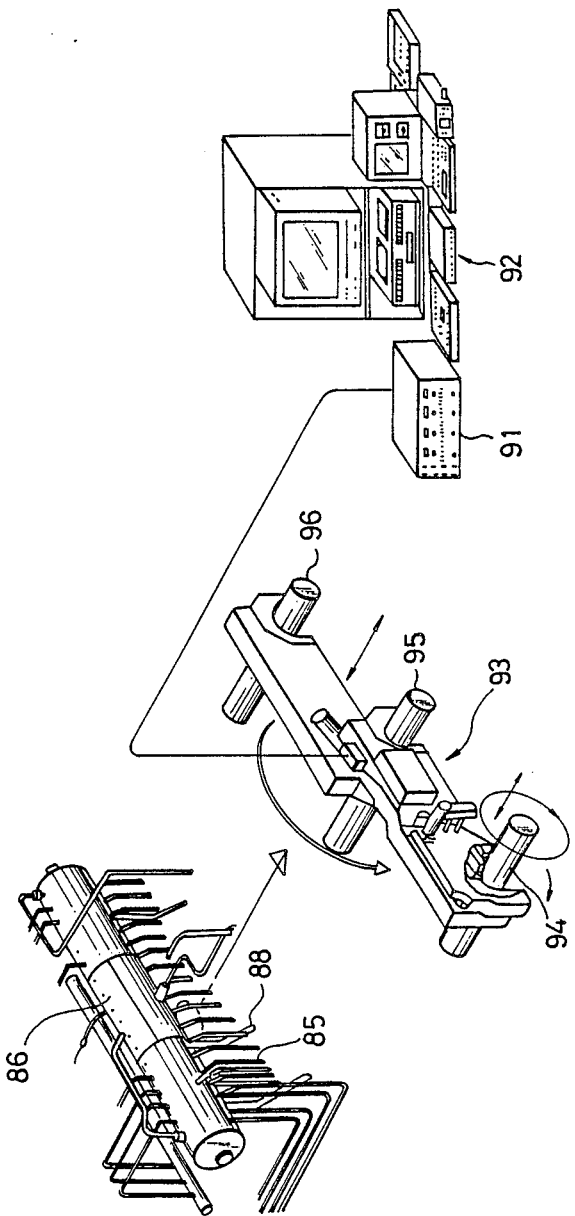
FIG. 9 is a view illustrating the overall arrangement of a remotely controlled, automatic examining apparatus for outlet pipes.
Figure 10:
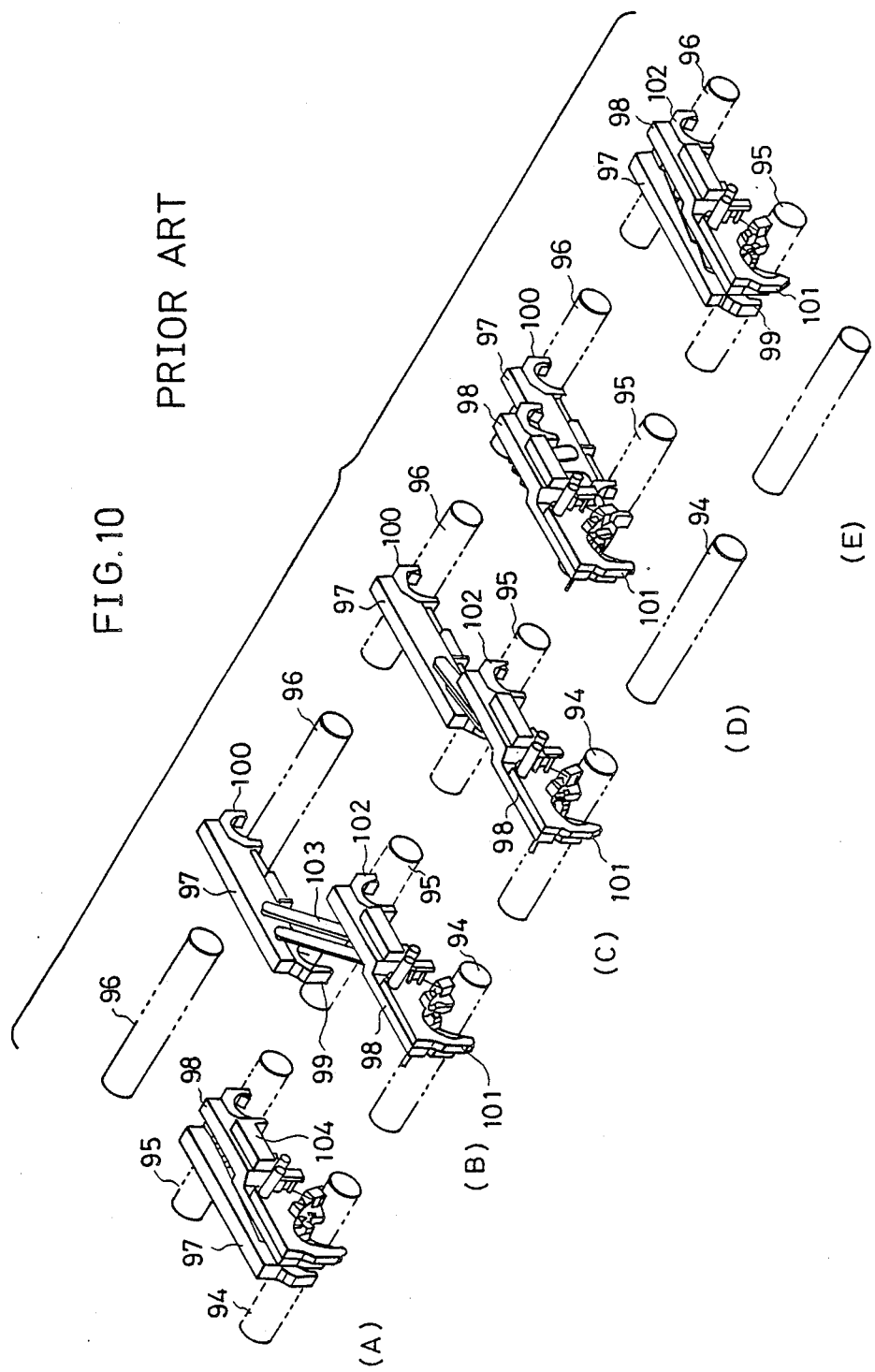
FIG. 10 illustrates the manner in which a mobile unit in FIG. 9 "walks" from one outlet pipe to another in accordance with the prior art.

FIG. 7 is a view illustrating the Y-axis drive mechanism. Portions similar to those shown in FIG. 4 are designated by like reference characters. Numeral 71 denotes a DC motor 72, a gear and a 73 a ball screw.

The Y-drive mechanism comprises the two bodies 37, 38 slidable relative to each other to extend or shorten the length of the mechanism. Specifically, the output shaft of the Y-axis drive DC motor 71 rotates the ball screw 73 via the gear 72, thereby extending or shortening the overall length of the bodies 37, 38 along the Y axis.

When an examination is made, the clamping mechanisms are made to clamp the pipe and the clamping device having the sensors provided on its side is moved axially of the pipe in the unclamped state (at a traveling speed of e.g. 50–$\phi$mm/min). The end of the stroke is detected by a microswitch, with motion along the Y axis being halted automatically in response to actuation of the microswitch. The position along the Y axis is detected by an encoder attached to the rearward portion of the DC motor 71. A pulse signal from the decoder is applied to the control unit to digitally display the position on the display device of the control panel.

When the examination apparatus moves while walking across pipes, any positional deviation that occurs along the Y axis is corrected by using the Y-axis drive mechanism to effect movement in the opposite direction along the Y axis by an amount equivalent to the deviation.

In the examination operation, the examination apparatus is made to scan a pipe in both the circumferential and axial directions thereof to perform visual, volume and other examinations. The results of these examinations are displayed on a display device (not shown) and subjected to data processing by a data processor (not shown).

The motions of the various components constituting the apparatus can be remotely controlled in both an automatic mode and a manual mode. It is also possible to adopt an arrangement in which the apparatus itself is provided with an internal microcomputer storing an examination sequence in accordance with which examination proceeds automatically.

In the embodiment described above, the examination apparatus is equipped with various sensors such as a TV camera and ultrasonic probe. However, it is obvious that other devices such as a welding jig or repair jig for pipe maintenance can also be mounted on the examination apparatus when required.

Thus, in accordance with the present invention as described above, the examination apparatus need only be mounted on a readily accessible location (an initially set position) on the outside of a group of pipes such as inlet or outlet pipes. Thereafter, the apparatus is made to walk automatically among the pipes by remote control from a control panel in an automatic or manual mode, or in response to control performed by a built-in microcomputer. This makes it possible to examine a large number of inlet and outlet pipes without requiring that this task be performed by workers. As a result, exposure to radiation can be greatly reduced in comparison with fault detection by hand. Whereas examining welds on the outsides of pipes and other regions not reachable by hand is difficult with the prior-art apparatus, these examinations can be performed by the apparatus of the present invention while the apparatus walks across the spaces among the pipes, thus making possible the inspection of all welds as well as the examination of a much wider area. Since the apparatus of the invention is capable of walking across pipes, the pipes can be traversed irrespective of the accuracy of the pitch at which the pipes are attached and even if the pitch differs. Since the motion of the clamping mechanisms when these clamp a pipe requires less space than in the prior art, examination can be performed over a wider range in the narrow spaces between pipes. Furthermore, since the apparatus is also capable of moving axially of a pipe, welds can be inspected even if the positions at which they are located are displaced from one another.

As many apparently widely different embodiments of the present invention can be made without departing from the spirit and scope thereof, it is to be understood that the invention is not limited to the specific embodiments thereof except as defined in the appended claims.

What we claim is:

1. An automatic pipe examination apparatus for scanning and examining at least one pipe, comprising:
    a pair of bodies slidable connected to each other such that the total length of the pair of bodies along a longitudinal axis thereof is adjustable;
    a first drive means for driving said pair of bodies along said longitudinal axial length;
    a pair of couplings each connected to one of said bodies in a manner such that each of said pair of couplings is movable with respect to one of said bodies within a first plane parallel to said longitudinal axis;
    a pair of second drive means for driving each of said pair of couplings within said first plane;
    a pair of gear boxes each connected to each of said pair of couplings in a manner such that each of said pair of gear boxes is movable with respect to said each of said pair of couplings within a second plane perpendicular to said first plane;
    a pair of third drive means for driving each of said pair of gear boxes within said second plane; and
    a pair of clamping devices each connected to each of said pair of gear boxes and each extending in a third plane substantially perpendicular to said longitudinal axis and to said second plane, each clamping device being provided with a clamping means for reasonably clamping said at least one pipe; and
    at least one scanning means movably positioned within at least one of said clamping device for examining the circumferential surfaces of said pipe.

2. The apparatus according to claim 1, wherein said scanning means includes various sensors such as a TV camera and an ultrasonic probe.

3. The apparatus according to claim 1, wherein said scanning means includes a welding jig and a repair jig.

4. The apparatus according to claim 1, wherein said scanning device is driven circumferentially of a pipe by a C-shaped gear meshing with a pinion driven by a motor through a timing belt.

5. The apparatus according to claim 4, wherein said pinion includes a plurality of pinions and at least one of said pinions is meshing with the C-shaped gear all the time.

6. The apparatus according to claim 1, wherein said scanning means is driven axially of a pipe by a ball screw driven by a motor.

7. The apparatus according to claim 1, wherein each of said clamping devices clamps a pipe by clamping claws actuated via a rack shaft driven by an air cylinder.

8. The apparatus according to claim 10, wherein said clamping devices are lifted up and lowered down by rotating a lift shaft and each end of said slidable bodies in opposite directions through identical angles by a motor acting through a spline shaft.

9. The apparatus according to claim 1, wherein said clamping devices are swung by rotating a first swing shaft by a motor and rotating a second swing shaft in an opposite direction of said first swing shaft through an identical angle by said motor acting through a flexible shaft.

* * * * *